(12) United States Patent
Vermeulen

(10) Patent No.: US 12,245,909 B2
(45) Date of Patent: Mar. 11, 2025

(54) MOUTHPIECE COMPONENT AND METHOD OF MANUFACTURE

(71) Applicant: KONINKLIJKE PHILIPS N.V., Eindhoven (NL)

(72) Inventor: Olaf Thomas Johan Antonie Vermeulen, Oss (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 534 days.

(21) Appl. No.: 17/611,738

(22) PCT Filed: May 13, 2020

(86) PCT No.: PCT/EP2020/063270
§ 371 (c)(1),
(2) Date: Nov. 16, 2021

(87) PCT Pub. No.: WO2020/229511
PCT Pub. Date: Nov. 19, 2020

(65) Prior Publication Data
US 2022/0233292 A1  Jul. 28, 2022

(30) Foreign Application Priority Data
May 16, 2019 (EP) ..................... 19174872

(51) Int. Cl.
*A61C 19/06* (2006.01)
*A61B 1/07* (2006.01)
*F21V 8/00* (2006.01)

(52) U.S. Cl.
CPC .............. *A61C 19/066* (2013.01); *A61B 1/07* (2013.01); *G02B 6/0055* (2013.01)

(58) Field of Classification Search
CPC ....... A61C 19/066; A61C 17/084; A61B 1/07; G02B 6/0055; G02B 6/0041; G02B 6/0045; G02B 6/0075; G02B 6/0078
See application file for complete search history.

(56) References Cited

U.S. PATENT DOCUMENTS

| 4,790,752 A | 12/1988 | Cheslak | |
| 2008/0131836 A1* | 6/2008 | Rueggeberg | A61B 1/24 433/29 |
| 2018/0256916 A1 | 9/2018 | Kothari | |

FOREIGN PATENT DOCUMENTS

| KR | 100773379 B1 | 11/2007 |
| WO | WO2005010585 A1 | 2/2005 |

(Continued)

OTHER PUBLICATIONS

PCT International Search Report, International application No. PCT/EP2020/063270, May 13, 2020.

*Primary Examiner* — Nicholas D Lucchesi

(57) ABSTRACT

There is disclosed a mouthpiece component for use in an intra oral illumination system, the mouthpiece component comprising a core structure which defines at least one waveguide for receiving light which is directable at least partly by the waveguide along at least one light path of the core structure, wherein each at least one light path defines a propagation direction for light in a propagation plane; at least one optical discontinuity which is configured to cause at least a portion of light propagating along the light path in the at least one waveguide to be transmitted out of the at least one core structure and continue to propagate substantially parallel to the propagation plane; and at least one light redirection portion which is configured to redirect at least a portion of light which has been transmitted out of the core structure out of the propagation plane. A method of manufacture thereof is also disclosed.

3 Claims, 9 Drawing Sheets

(56) References Cited

FOREIGN PATENT DOCUMENTS

| | | |
|---|---|---|
| WO | WO2006128021 A2 | 11/2006 |
| WO | WO2010124028 A2 | 10/2010 |
| WO | WO2018130621 A1 | 7/2018 |
| WO | WO2018177795 A1 | 10/2018 |

\* cited by examiner

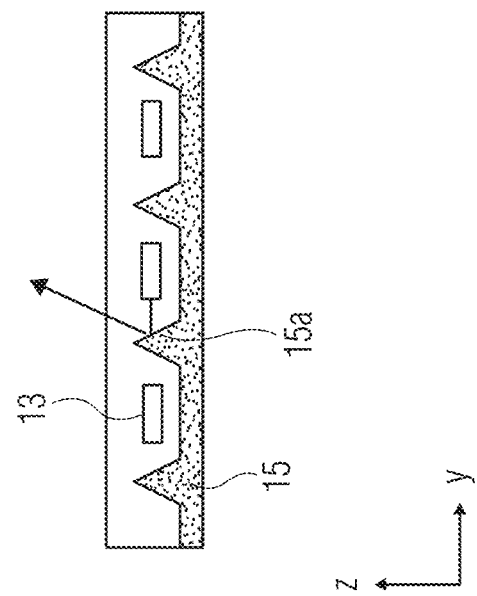
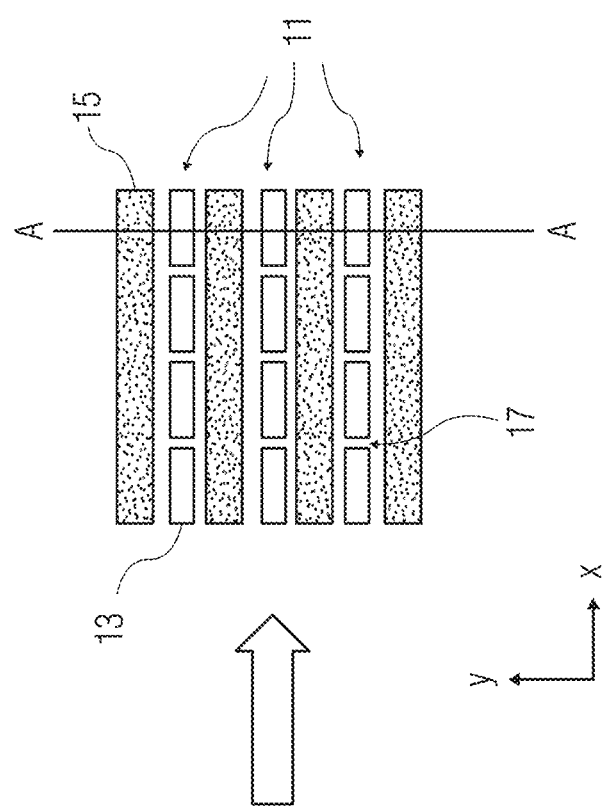
FIG. 4B
FIG. 4A

MOUTHPIECE COMPONENT AND METHOD OF MANUFACTURE

This application is the U.S. National Phase application under 35 U.S.C. § 371 of International Application No. PCT/EP2020/063270, filed on May 13, 2020, which claims the benefit of European Application Serial No. 19174872.2, filed May 16, 2019. These applications are hereby incorporated by reference herein.

FIELD OF INVENTION

This invention relates to a component for use in an intra-oral illumination system, and particularly but not exclusively relates to a component of a mouthpiece for use in an intra-oral illumination system, such as a dental illumination system or an intra-oral detection system.

BACKGROUND OF THE INVENTION

Intra-oral illumination systems use light to illuminate parts within an oral cavity, for example the teeth, the gums, a part of the buccal cavity, the roof of the mouth, a tongue, throat etc. One type of intra-oral illumination system is a dental illumination system which is used to irradiate teeth with light, for example to whiten teeth of a user. These systems usually comprise a light source and a mouthpiece, where a whitening agent is applied to the teeth of a user, and light is then emitted to the teeth via the mouthpiece to accelerate or activate the whitening process.

The mouthpieces are used to distribute light across users' mouths. However, mouthpieces do not always provide an even distribution of light which is required for even tooth whitening. For example, a mouthpiece which uses point sources as light sources, such as LEDs, may cause non uniformity of illumination which creates 'hotspots' (regions with higher irradiance levels) on the dental arch, thereby negatively affecting the whitening process. A further complication is that the intensity levels of light at the teeth are strongly dependent on the source to tooth distance. Thus, whitening systems often do not have enough light output to be effective, or are not able to deliver homogenous distributed light toward the teeth.

Other existing tooth whitening systems which use light assistance use a lamp positioned over the open mouth of a user. This provides high output levels of homogeneous light, but restricts the user from free movement.

SUMMARY OF THE INVENTION

It would be advantageous to provide a component of a mouthpiece for a tooth whitening system that provides an improved light distribution. To better address these concerns, there is provided a mouthpiece component for use in an intra-oral illumination system (e.g. dental illumination system, intra-oral detection system, etc.), the mouthpiece component comprising a core structure which defines at least one waveguide for receiving light which is directable at least partly by the waveguide along at least one light path of the core structure, wherein each at least one light path defines a propagation direction for light in a propagation plane (which may be substantially parallel to teeth of a user in use); at least one optical discontinuity which is configured to cause at least a portion of light propagating along the light path in the at least one waveguide to be transmitted out of the at least one core structure and continue to propagate substantially parallel to the propagation plane (e.g. teeth of the user in use); and at least one light redirection portion which is configured to redirect at least a portion of light which has been transmitted out of the core structure out of the propagation plane (e.g. towards the teeth of a user in use).

Thus, a portion of light may be transmitted out of the core structure, and a portion of light may continue to propagate through the core structure. Therefore, a more even distribution of light throughout the core structure may be achieved, which may lead to an improved distribution of light on the teeth of a user. For example, the light may be extracted such that extracted light provides an evenly distributed light pattern. The even distribution may be further enabled by having light redirection elements redirect extracted light.

The optical discontinuity may comprise an interface between the core structure and its immediate surroundings which have a different refractive index to the core structure, wherein the interface may be configured to cause a portion of light propagating along the light path and incident on the interface to be transmitted out of the core structure.

The interface may comprise at least one of: a texture, shape, and an angle with respect to the propagation plane of the light path. Thus, the interface may be configured so as to break the total internal reflection which confines the light in the waveguide. The interface may be in a plane normal to the propagation direction of light along the light path. Thus, the angle of light incident on the interface may be less than the critical angle, causing the light to be directed out of the core structure. The interface may define an interface between the core structure and a material having a different refractive index to the core structure which causes light incident on the interface to be transmitted out of the core structure.

The at least one waveguide may comprise a first waveguide and a second waveguide which define a first light path and a second light path respectively, and wherein the first light path and the second light path may intersect at an intersection portion, wherein the optical discontinuity may be comprised in or is adjacent to the intersection portion. The intersection may be a portion of the component which intercepts both a first waveguide and a second waveguide. The first light path may define a general propagation direction of light through a waveguide of the core structure, and/or a general direction of propagation of light through the core structure. The first waveguide and the second waveguide may be angled with respect to one another and be formed in the same plane, overlapping at an intersection portion. The first light path may be a direction in which light propagates through the first waveguide, and the second light path may be a direction in which light propagates through the second waveguide. The first light path and the second light path may be angled with respect to one another. The light path may be a direction which is partly defined by the structure of the waveguide, and partly from the coupling of light into the core structure. The first light path of the first waveguide may be defined as progressing in a direction along a first waveguide portion, through the intersection portion and continuing along a second waveguide portion. The second light path of the second waveguide may be defined as progressing in a direction along a first waveguide portion, through the intersection portion and continuing along the second waveguide portion.

The at least one optical discontinuity may comprise an optical gap between a first portion of the core structure and a second portion of the core structure. For example, the optical gap may define a separation between portions of the waveguide structure. The optical gap may have a different refractive index to the core structure. Thus, the optical gap may comprise material having a different refractive index to the core structure. Light propagating along the waveguide may be diverted out of the light path at the optical discontinuity.

The intersection portion of the first waveguide and the second waveguide may comprise at least one of: the optical gap; material having the same refractive index as the core structure. For example, the intersection portion may be devoid of core structure material.

A shape of the intersection portion in a plane defined by the first and second waveguides may comprise at least one of: a circle, an octagon, a square, a diamond, an ellipse, any other polygonal shape. The shape of the intersection portion may increase the number of surfaces which are angled with respect to the propagation direction of light. Thus, more light may be coupled out of the core structure via the intersection portion, leading to a higher intensity of light being directed towards the teeth of the user.

The light redirection portion may redirect the light by at least one of: reflection from a reflective surface; refraction; and total internal reflection. The reflective surface may comprise at least one of: a diffuse reflective surface; a specular reflective surface.

The light redirection portion may comprise at least one redirection structure. The redirection structure may be chosen from a group comprising: a pyramid, a cube, a cuboid, another polyhedral shape, a sphere, a hemisphere and a grid.

According to a further aspect, a mouthpiece for use in intra-oral illumination may be provided comprising the mouthpiece component.

According to a further aspect, there may be provided an intra-oral illumination system comprising the mouthpiece component, and/or the mouthpiece, and may further comprise a light source for directing light into the core structure in the propagation direction. The light source may be positioned so as to be external to the mouth of the user in use. Use of a remote light source may provide the benefit that the component or even the mouthpiece does not have to cope with heat created by the light source.

According to a further aspect, there may be provided a method for manufacturing the mouthpiece component, wherein the method comprises the following steps: forming a redirection layer comprising at least one light redirection portion; forming a first cladding layer over the redirection layer; forming the core structure comprising at least one optical discontinuity at the first cladding layer; and forming a second cladding layer over the core structure.

BRIEF DESCRIPTION OF THE DRAWINGS

Embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

FIGS. 4A and 4B illustrate a component according to an example;

DETAILED DESCRIPTION OF EMBODIMENTS

Figure 1:
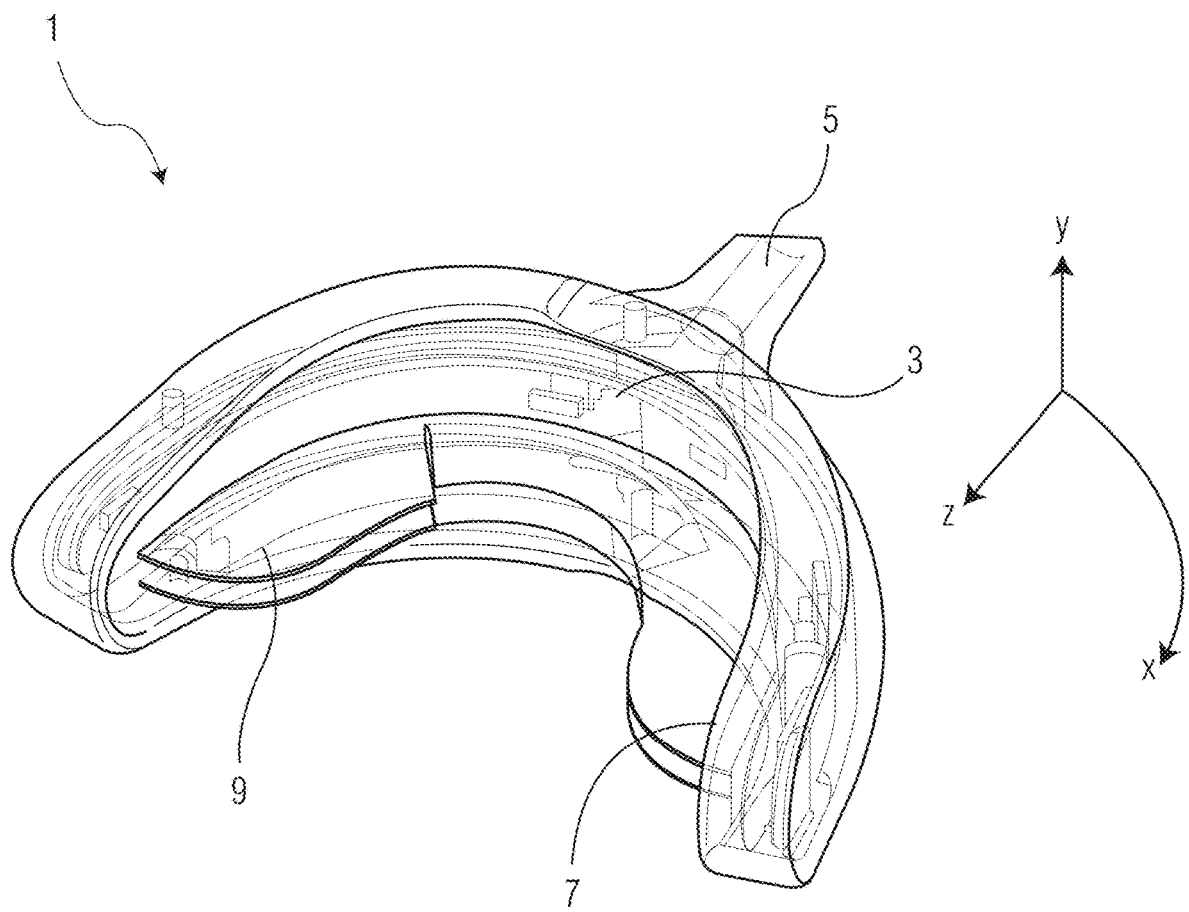
FIG. 1 illustrates a mouthpiece comprising a component according to an example.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

FIG. 1 shows a mouthpiece 1 for use in a teeth illumination device according to an example. In the examples described herein, the illumination device is used to illuminate the teeth of a user. However, it should be appreciated that the mouthpiece component described herein may be used for any purpose to illuminate any part of an oral cavity of a user, for example, the gums, a part of the buccal cavity, the roof of the mouth, a tongue, throat etc. The teeth of a user may be illuminated for the purpose of teeth whitening, plaque or bacteria hygiene, or other oral hygiene or care uses. The mouthpiece may be a consumer product for home use or a professional product to be used by a professional, in both cases the user, i.e. the home user or the patient, is the person that receives the illumination from the device.

The mouthpiece 1 comprises a component 3 which is arranged to face, and to transmit light which has been coupled into the component, to the buccal side of the teeth of a user (e.g. towards the teeth of a user in use). For example, the light may propagate through the component in a direction which is substantially parallel to the teeth of the user (in an x-y plane) until it is diverted out of the component and subsequently travels towards the teeth of the user (in a z direction). The mouthpiece 1 comprises the component 3 which comprises a waveguide, a light source 5 arranged for injecting light into the component, and an optically transparent element 7 arranged to contact the component. There may be provided a plurality of light sources. Each light source may inject light into the component in a different direction. The optically transparent element 7 has a lower refractive index than the core structure to enable total internal refection of the injected light in the core structure. Light is diverted out of the light guide by light redirection means and through a part of the optically transparent element located between the component and the buccal side of the teeth to illuminate the teeth with uniform light.

According to an example, the mouthpiece 1 comprises a protruding bite part 9 extending along at least a part of the optically transparent element 7. The bite part 9 extends outwardly to form upper and lower bite surfaces above and below the plane of the bite part 9. The user can bite onto the upper and lower bite surfaces so that the upper and lower occlusal sides of the teeth contact the bite surfaces. In this way the mouthpiece can be held in place in the mouth by applying a force from the teeth to the bite part 9.

The optically transparent element 7 may be made from elastic materials like silicone or similar materials. For example, the optically transparent element 7 may be made from transparent silicone or another transparent polysiloxane polymer. The optically transparent element 7 may be formed as a one-piece body, e.g. a one-piece body moulded from a single material.

The optically transparent element 7 is referred to as a transparent part, i.e. transparent in the sense that the light is not scattered in the optically transparent element. However, in practice the transparent material of the teeth may contain irregularities, e.g. particles, implying that some light scattering may take place. Accordingly, the optically transparent element may in practice be an optically translucent element.

Figure 2:
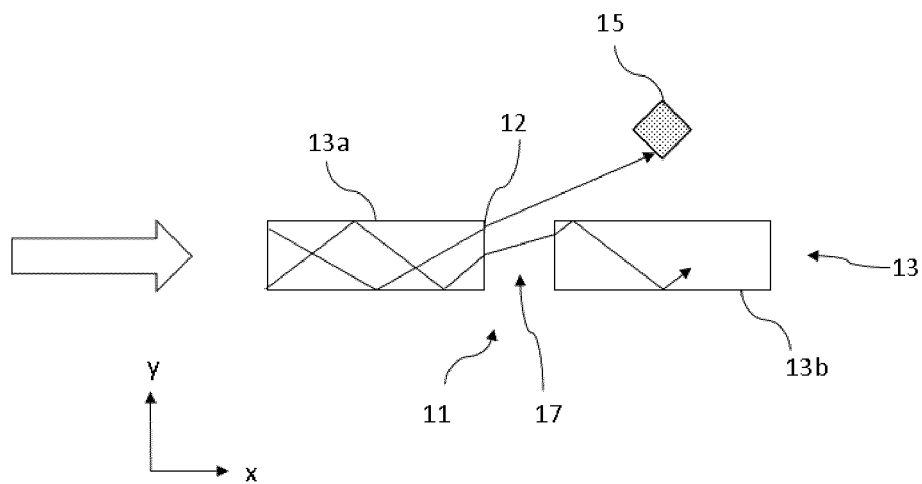
FIG. 2 illustrates propagation of light though the component in an x-y plane according to an example.

Referring to FIG. 2, the component 3 comprises a core structure 11 extending along the optically transparent element 7 and connected to one or more light sources arranged for injecting light into the core structure. The core structure 11 has a refractive index which is higher than the refractive index of optically transparent element 7 to enable total internal refection of the injected light at locations where the core structure 11 contacts the optically transparent element 7. For example, the core structure 11 may be made from flexible, high refractive index polymer materials, for example LIGHTLINK™ XP-6701A, which has a higher refractive index than the material of at least the optically transparent element 7, which may also be made from silicone. Alternative materials for the core structure 11 includes polycarbonate, polymethylmethacrylat, cyclic-olefin polymers, cyclic-olefin copolymers, polyetherimide, styrene and polyesters such as OKP-4.

FIG. 2 illustrates a portion of the component according to an example. The component comprises a core structure 11 comprising a waveguide 13. In the following examples, the core structure is surrounded by a cladding material, however, the core structure may be at least partly surrounded by any material having a different refractive index to the core structure, in the form of a solid, liquid or gas. The cladding material is a material having a different refractive index to that of the core structure, and in the following examples has a lower refractive index than that of the core structure. Light is coupled into the core structure by at least one light source. For example, each light source may inject light into the waveguide of the component. The waveguide is arranged so as to guide light in a direction which extends substantially parallel to, or wraps around, the teeth of a user in use (in the x-y plane shown in FIG. 2). In this example, the waveguide comprises a first waveguide portion 13a and a second waveguide portion 13b. Light propagating through the first waveguide portion 13a in the direction which is parallel to the teeth of the user is incident on an optical discontinuity 17. The optical discontinuity is situated between the first waveguide portion 13a and the second waveguide portion 13b, and is arranged so as to interrupt a light path (the direction of light paths herein are indicated with block arrows), which defines a propagation direction for light in a plane which is substantially parallel to teeth of a user in use. Light will propagate through a waveguide in a direction which is partly defined by the shape of the waveguide, and partly defined by the coupling of light from the light source into the component.

Light propagating through the first waveguide portion 13a which is incident on surfaces which are in a plane which is angled with respect to a general propagation direction of light at an angle greater than the critical angle $\theta_{crit}$ will be totally internally reflected, due to the angle of incidence and the difference in refractive index between the core structure and the surrounding material. For example, sides of the core structure which are substantially parallel to the propagation direction of light will cause light to be totally internally reflected. The critical angle of light propagating through the core structure may be calculated as follows using the refractive index of the core structure ($n_1$) and refractive index of the surrounding material (which may be the optical discontinuity) ($n_2$):

$$\theta_{crit} = \arcsin\frac{n_2}{n_1}$$

Thus, light propagating through the waveguide 13 will generally be incident on sides of the core structure at an angle greater than the critical angle, as the sides of the core structure on which light will be incident in the waveguide 13 will be substantially parallel to the direction of propagation of light (in the x direction), and will thus be totally internally reflected. The optical discontinuity 17 is arranged so as to break this total internal reflection. This may be the result of a texture of an interface between the optical discontinuity and the first portion of the waveguide, and/or a shape of the interface, and/or the angle of the interface with respect to the propagation direction of light, and/or the result of the difference in refractive index of the optical discontinuity and the core material. In this example, the interface comprises a surface 12 which is arranged so as to be in a plane which is perpendicular to the overall direction of travel of light, and perpendicular to a plane parallel to the teeth of the user in use. The optical discontinuity is formed of a material with a different refractive index to that of the core structure, which may be the same as the cladding material.

The interface between the optical discontinuity 17 and the waveguide 13 extends in this example at 90° with respect to the propagation direction of light. Light which is incident on the interface will therefore likely be transmitted out of the first waveguide portion 13a, as the angle of incidence will likely be less than the critical angle. The light which has exited the first waveguide portion 13a will remain travelling in a direction which is substantially parallel to the teeth of the user, although the angle of travel of light may be altered within the plane parallel to the teeth of the user (the x-y plane). Thus, the optical discontinuity is configured to cause at least a portion of light propagating along the light path in the waveguide to be transmitted out of the waveguide and continue to propagate substantially in a direction parallel to the teeth of the user.

It will be appreciated that various angles of the interface with respect to the plane of the general direction of propagation of light could be used to produce the same result of a portion of light being transmitted through the interface, depending on the relative refractive indexes of the materials adjacent to the core structure and the core structure itself.

As is described above, and as is shown in FIG. 2, light propagating through the waveguide which is incident on the interface will likely be at an angle which is less than the critical angle of the interface, and this light will thus travel through the interface (out of the core structure or waveguide) and into the optical discontinuity. A portion of light which has been transmitted out of the first waveguide portion 13a will be incident on an interface between the second waveguide portion 13b and the optical discontinuity, and will thus travel into the second waveguide portion 13b (e.g., continue to propagate along the waveguide 13). In the same way as described with respect to the first waveguide portion 13a, light which has travelled into the second waveguide portion 13b may be subject to total internal reflection. In this case, a portion of light will continue to propagate through the waveguide (or core structure), in the second waveguide portion 13b, in a direction which is substantially parallel to the teeth of the user in use.

By introducing one or more optical discontinuities so as to interrupt the path of light in the component, a portion of light will be diverted out of the core structure, and a portion of light will continue to propagate through the core structure, thus improving the distribution of light leaving the mouthpiece. Furthermore, a portion of light which is diverted out of the core structure may be directed out of the plane of propagation of light, and instead be directed towards the teeth of the user. This configuration may create a high intensity/low dissipating large diffuse surface emitter. This may additionally allow the light source to be provided outside the mouth, where light is coupled into the mouthpiece, and into the waveguide. This may allow more power to be provided to the light source as the light sources are outside the mouth.

Figure 3:
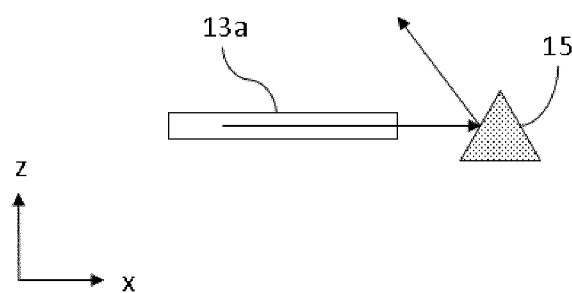
FIG. 3 illustrate propagation of light through the component of FIG. 2 in an x-z plane.

Referring to FIG. 3, a portion of light which has travelled out of the first waveguide portion 13a will be incident on the redirection portion 15. The light incident on a redirection portion 15 will be redirected out of the plane substantially parallel to the teeth of the user, towards the teeth of the user (substantially in the z direction shown in FIG. 3). Light redirected towards the teeth of the user may travel through the optically transparent element 7 to the teeth of the user. The redirection portion may be particularly beneficial in extracting light which would otherwise continue to be transmitted in and out of the core structure without being directed towards the teeth of the user. For example, light which is propagating through the waveguide in a direction substantially parallel to the teeth of the user in use may not be diverted towards the teeth of the user (z axis) by entering and leaving the core structure, as the direction may only vary in the x-y plane. Thus, the redirection structure may increase the amount of light which is transmitted out of the core structure, and thus increase the intensity of light on a user's teeth. Additionally, the redirection portion may serve to divert incident light in different directions, thereby resulting in a more even, or uniform, distribution of light.

The redirection portion may comprise a redirection structure which interrupts the plane of propagation of light. For example, the redirection structure may be a pyramid shaped structure, which has a surface angled with respect to the plane of propagation of light. The redirection structure may comprise any structure which is able to divert light. For example, the redirection structure may comprise any of a prism, cube, a cuboid, another polyhedral shape, a sphere, a hemisphere and a grid. The redirection structure may be a triangular prism which is arranged parallel to a plurality of waveguide portions. A redirection surface 15a of the redirection structure may be reflective such that light incident on the surface is reflected towards the teeth of the user. Alternatively or additionally, the redirection portion may comprise material which is able to refract light, and thereby be able to direct a portion of light towards the teeth of the user. The redirection portion may comprise a planar surface which is provided with at least one redirection structure.

FIGS. 4A and 4B show a further example of a mouthpiece component. In this component, there is provided a core structure 11 providing a plurality of waveguides 13. Each waveguide 13 is separated into a plurality of waveguide portions, each portion separated from the adjacent portion by an optical discontinuity 17. Light which is coupled into the waveguides 13 propagates in an x direction in the same manner as described for the aforementioned Figures. A plurality of redirection portions 15 extend parallel to the waveguides. The redirection portions shown in this example are elongate, triangular prism shaped, redirection portions provided along the length of the waveguide. A cut through portion along line A-A is shown in FIG. 4B. As is shown here, the redirection portions comprise a redirection surface 15 a which is in a plane which is angled with respect to the x-y plane, and the waveguides are arranged between the redirection portions. As discussed above, a portion of light propagating substantially in the direction x in the x-y plane will be coupled out of a waveguide portion, and may be incident on a redirection portion. The redirection portion is configured (angled) to redirect the light as discussed above, such that at least a portion of light exiting the core structure is directed towards the teeth of the user (in the z direction).

Figure 5:
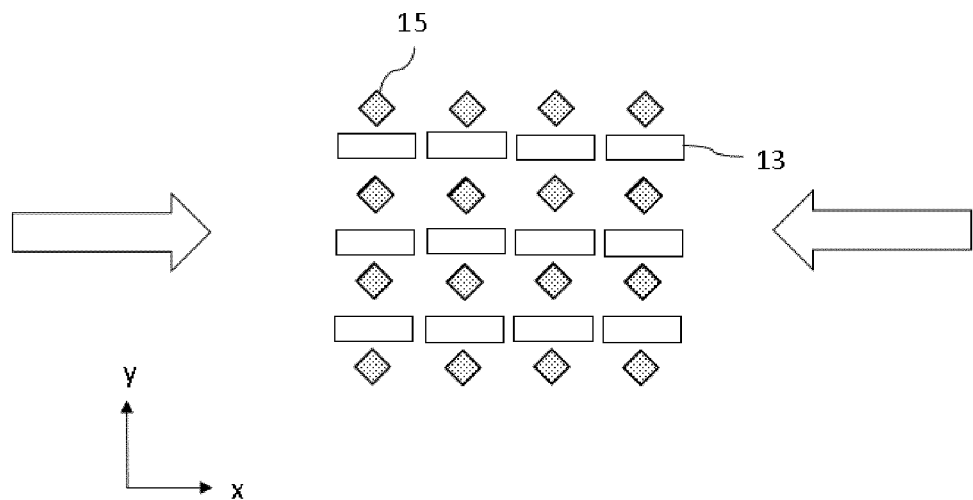
FIG. 5 illustrates a component according to an example.

Another example of a possible configuration of the redirection portions is illustrated in FIG. 5. This figure illustrates a component which comprises a plurality of redirection portions 15. The redirection portions are similarly arranged to the redirection portions of FIG. 4B, where redirection portions are situated between a plurality of waveguides 13. The redirection portions in this example are pyramidal in shape. The pyramidal shape provides redirection surfaces which are angled with respect to the plane of propagation of light through the core structure. A portion of light propagating through the waveguides may be transmitted out of the core structure at an optical discontinuity between waveguide portions, and propagate in a direction which is incident on a redirection portion. A portion of light incident on the redirection portion may be redirected from a direction of propagation in a plane parallel to the teeth of a user in use, and instead will be directed towards the teeth of the user in use. The redirection portions are arranged periodically, where each redirection portion is situated adjacent to a portion of core structure, similarly to the configuration shown in FIGS. 2 and 3.

Figure 6:
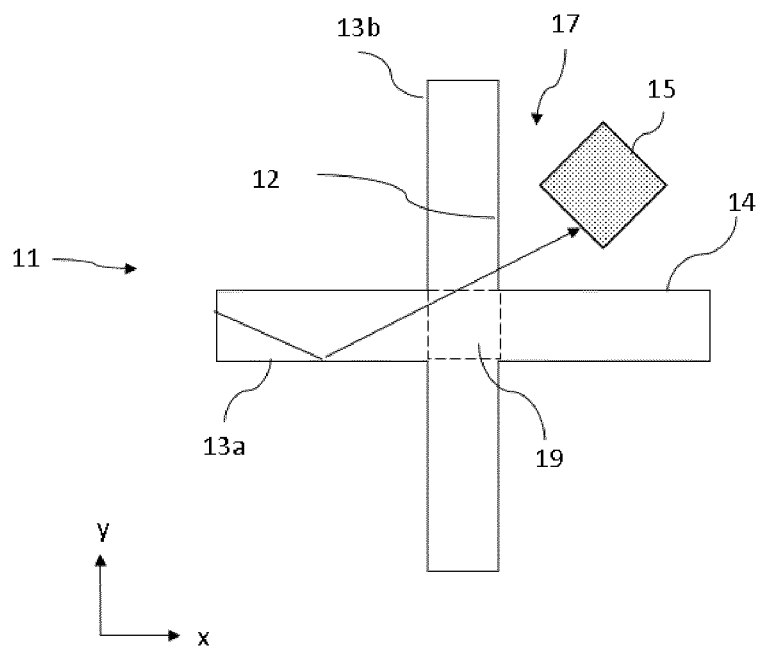
FIG. 6 illustrates a component according to an example.

FIG. 6 shows a further example of a component. In this example, the component comprises a core structure 11 provided with a first waveguide 13a and a second waveguide 13b which intersect at an intersection portion 19. The intersection portion 19 is a region situated between a first and second portion of the first waveguide 13a and is situated between a first and second portion of the second waveguide 13b. A portion of light propagating through the first waveguide 13a substantially in the x direction (in a first light path) and passing through the intersection portion 19 will be incident on a side wall of the second waveguide 13b as illustrated in this figure. An optical discontinuity 17 (in this case, a material with a different refractive index to that of the core structure) is situated adjacent to the first and second waveguides. The angle of a side wall of the first waveguide 14 which is adjacent to the optical discontinuity is in a plane parallel to the direction of light in the first light path (x direction). However, the angle of the side wall of the second waveguide 12 which is adjacent to the optical discontinuity is in a plane normal to the general direction of light propagating along the first light path (x direction). Light propagating through the first waveguide in the first light path will therefore be totally internally reflected when incident on side walls of the first waveguide. However, when light which is propagating in the first light path is incident on a side wall of the second waveguide, the angle at which the light will be incident on the side wall of the second waveguide may therefore be less than the critical angle, resulting in a portion of light being transmitted out of the core structure. A portion of light transmitted out of the core structure in this manner may be incident on a redirection portion 15, as described above.

In any of the examples herein, it will be appreciated that light may be coupled into the core structure in any direction. For example, the light may be coupled into the first waveguide so that light propagates along the first waveguide in a positive x direction. Alternatively or additionally, light may also be coupled into the waveguide so that light propagates along the first waveguide in a negative x direction. Similarly, light may be coupled into the second waveguide in a positive y and/or negative y direction. Light may therefore propagate through the waveguides in all or some of the aforementioned directions. Therefore, in the example above, light propagating in the second waveguide may be coupled out of the core structure at a side wall of the first waveguide, similarly to the configuration described above. Where light is incident on a side wall of the core structure which is in a plane which is angled with respect to the general direction of propagation of light, the light may be transmitted out of the core structure.

Figure 7A:
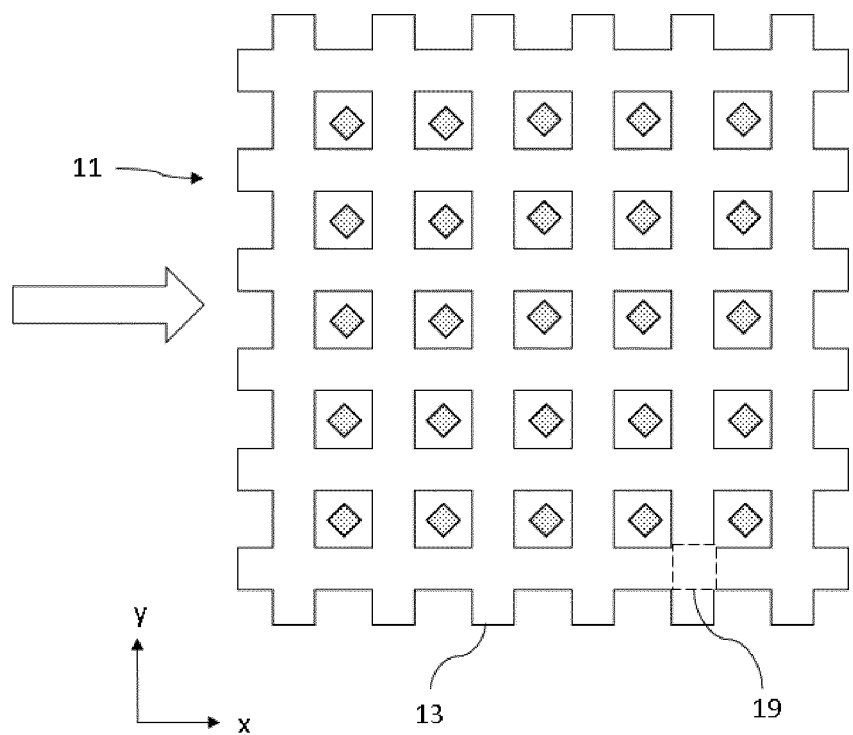
FIGS. 7A and 7B illustrate the configuration of the core structure of components according to an example.
Figure 7B:
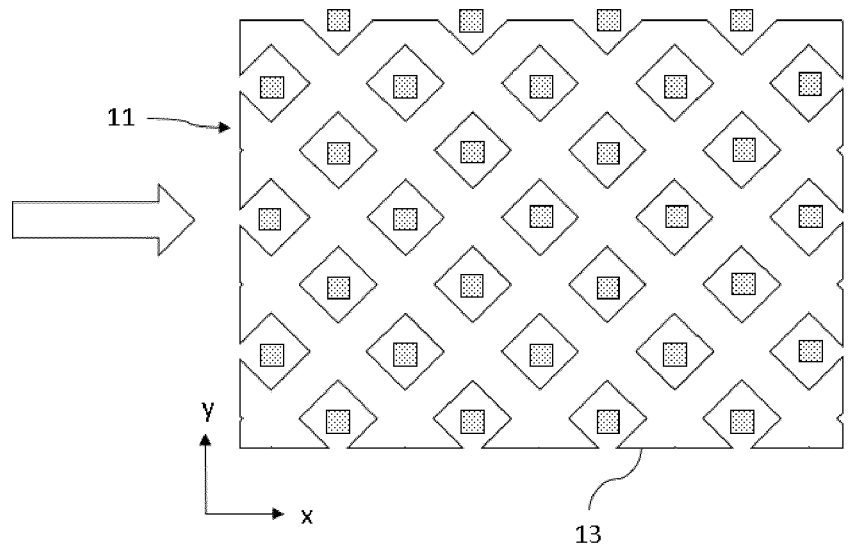

FIGS. 7A and 7B show some further configurations of a core structure comprising waveguides with intersection portions 19. FIG. 7A illustrates a plurality of waveguides which intersect at a plurality of intersection portions 19. In FIG. 7A, a first plurality of waveguides are arranged in the x direction. A second plurality of waveguides are arranged in the y direction (perpendicular to the first plurality of waveguides) in the same plane as the first plurality of waveguides, and the first plurality of waveguides intersect the second plurality of waveguides at intersection portions. Thus, the core structure is in the form of a grid. A plurality of redirection portions are arranged so as to intersect the plane of the waveguides, and are situated in regions outside of the core structure material defined by the grid structure. Light may be transmitted out of the core structure in the manner described in relation to FIG. 6. In this example, light is coupled into the core structure so as to propagate in the x direction. However, the light may be coupled into the core structure in any direction, for example, also in the +y and/or −y and/or −x directions.

FIG. 7B shows a similar configuration to FIG. 7A, but in this case the plurality of first waveguides are angled at −45° with respect to the x direction, and the plurality of second waveguides are angled at −45° with respect to the y direction (e.g., the structure of FIG. 7A is rotated about an angle of 45°). Light is coupled into the first and second waveguides in the x direction. Therefore, the plurality of first waveguides and the plurality of second waveguides are angled with respect to the direction of propagation of light. Thus, there is a higher probability that light propagating through the core structure will be incident on a surface which is angled with respect to the propagation direction in a manner that causes light to be transmitted out of the core structure. The light may be coupled into the core structure in any direction, for example, also in the +y and/or −y and/or −x directions.

Figure 7C:
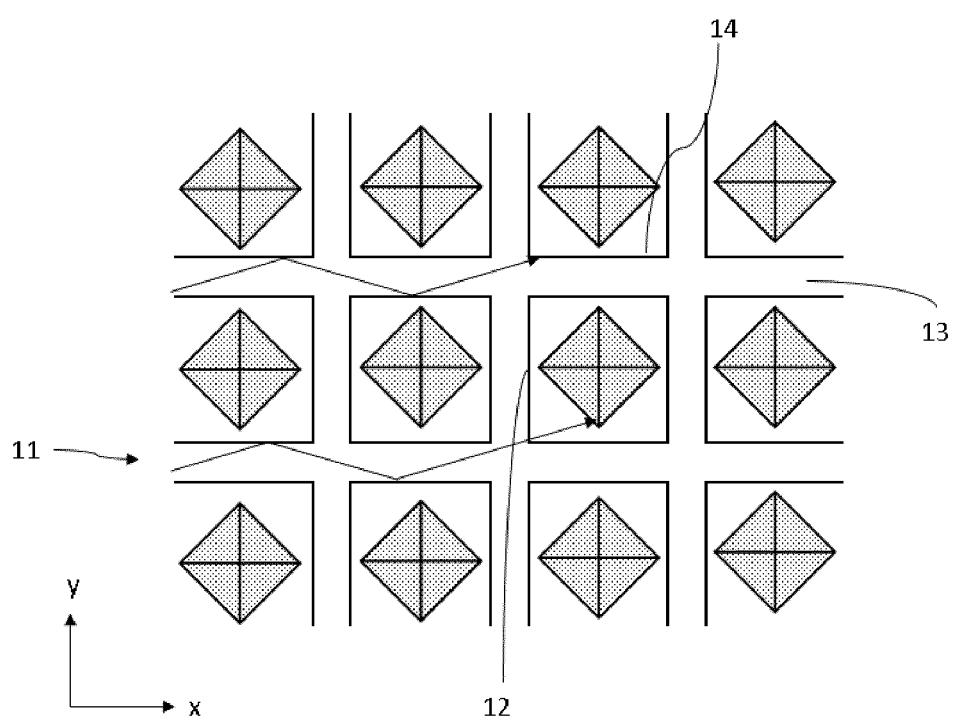
FIG. 7C illustrates the propagation of light through the component of FIG. 7A.

An example of propagation of light through the FIG. 7A structure is illustrated in FIG. 7C, which shows an extended version of the example shown in FIG. 6. As can be seen in this figure, light propagating in a general direction x (in the first light path) which is incident on a side wall of the plurality of waveguides 13 which is in a plane parallel to the propagation direction of light causes the light to be totally internally reflected. Light propagating in a general direction x (in the first light path) which is incident on a side wall 12 of the plurality of waveguides which is in a plane angled (in this example normal) with respect to the propagation direction of light causes the light to exit the core structure. Thus, any interface between the core structure and an optical discontinuity which is angled with respect to the propagation direction of light may result in light propagating through the core structure to be transmitted out of the core structure, but light may continue to propagate in a direction substantially parallel to the teeth of a user in use. A portion of the light which exits the core structure 11 may be incident on a redirection structure and consequently be directed out of the plane of propagation of the light towards the teeth of a user in use as discussed above.

Figure 8B:
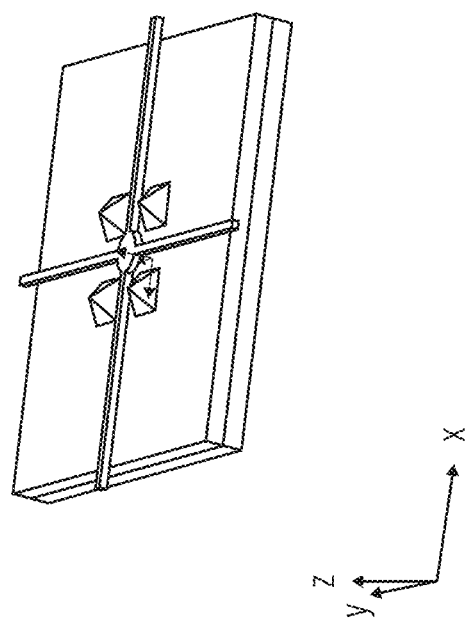
FIGS. 8A and 8B illustrate the configuration of intersection portions of a component according to an example.
Figure 8A:
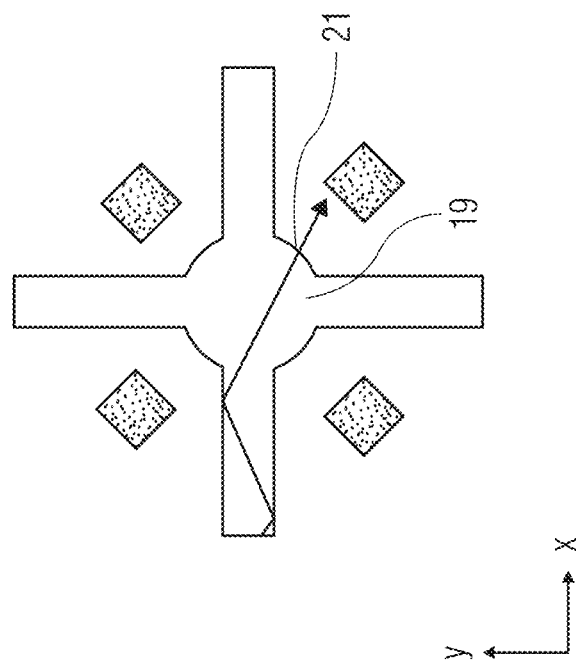

FIGS. 8A and 8B illustrate a further example where the intersection portion is shaped to facilitate the transmission of light out of the core structure. FIG. 8B illustrates a three dimensional representation of the image of FIG. 8A. The intersection portion FIGS. 8A and 8B in this example is cylindrical, where the circular face of the cylinder is arranged in the plane of the first and second waveguides (in a plane parallel to the teeth of a user). The cylindrical shape of the intersection portion provides additional side walls 21 to the overall core structure which are situated in a plane which is angled with respect to a propagation direction of light. For example, light propagating substantially in the x direction which is incident on a first side wall 21 of the intersection portion will likely be incident on the first side wall 21 at an angle which is less than the critical angle and, consequently, a portion of the light will be transmitted out of the core structure material. By providing additional surfaces (e.g. side walls 21) which interrupt the propagation path of the light, but which are situated in a plane which is angled with respect to a propagation direction of light, a greater portion of light which is propagating through the core structure will exit the core structure. This may ensure a greater intensity of light will be emitted towards the teeth of a user.

Figure 9:
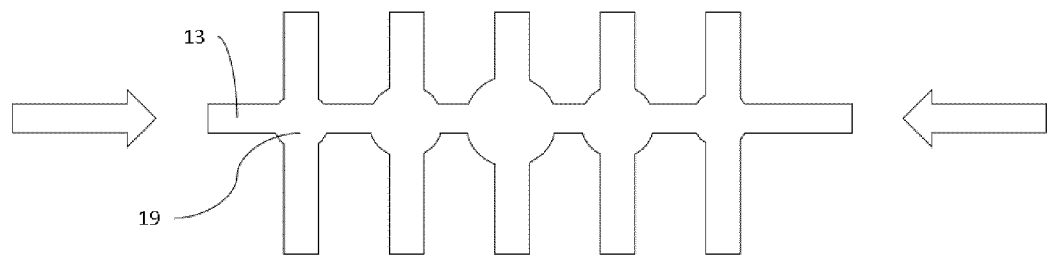
FIG. 9 illustrates a core structure comprising intersection portions according to an example.

FIG. 9 illustrates further examples of a possible arrangement of intersection portions 19. It should be appreciated that each intersection portion may differ in shape and/or structure from at least one other of the intersection portions. The shape/dimensions of the intersection portions may be selected so as to better distribute light throughout the mouthpiece component. In this example, the dimensions of the intersection portions are not all the same. For example, the intersection portions increase in size towards the centre of the waveguide 13, and then decrease in size from the centre of the waveguide to the end of the waveguide. As is shown in FIG. 9, light may be coupled into the waveguide from two opposing directions. The intersection portions which are closest to the coupling of the light are smaller to prevent a large amount of light from being transmitted out of the core structure towards the ends of the component, so that at least some of the light continues to propagate through the core structure. At a distance of the waveguide further from the coupling of light, the intersection portions are larger which may ensure that, while the amount of light propagating though the core structure further from the coupling may be lower, a similar amount of light is able to be coupled out of the core structure and can subsequently be directed towards the teeth of a user. Thus, at a distance which is mid-way between the coupling of light, the intersection portion is largest, and will serve to couple a large amount of the remaining light out of the core structure. Thus, the intersection portions may be formed so as to cause more evenly distributed coupling of light out of the core structure.

Figure 10:
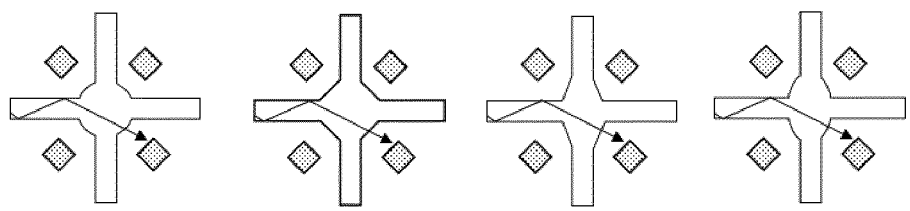
FIG. 10 illustrates different configurations of intersection portions of core structures according to an example.

FIG. 10 shows various alternative shapes in which the intersection portion may be formed. For example, the intersection portion may be circular, octagonal, square, diamond shaped, elliptical, or any other polygonal shape in a plane defined by the first and second waveguides. The intersection may be formed of any number of side walls which are angled with respect to the propagation direction of light.

Figure 11:
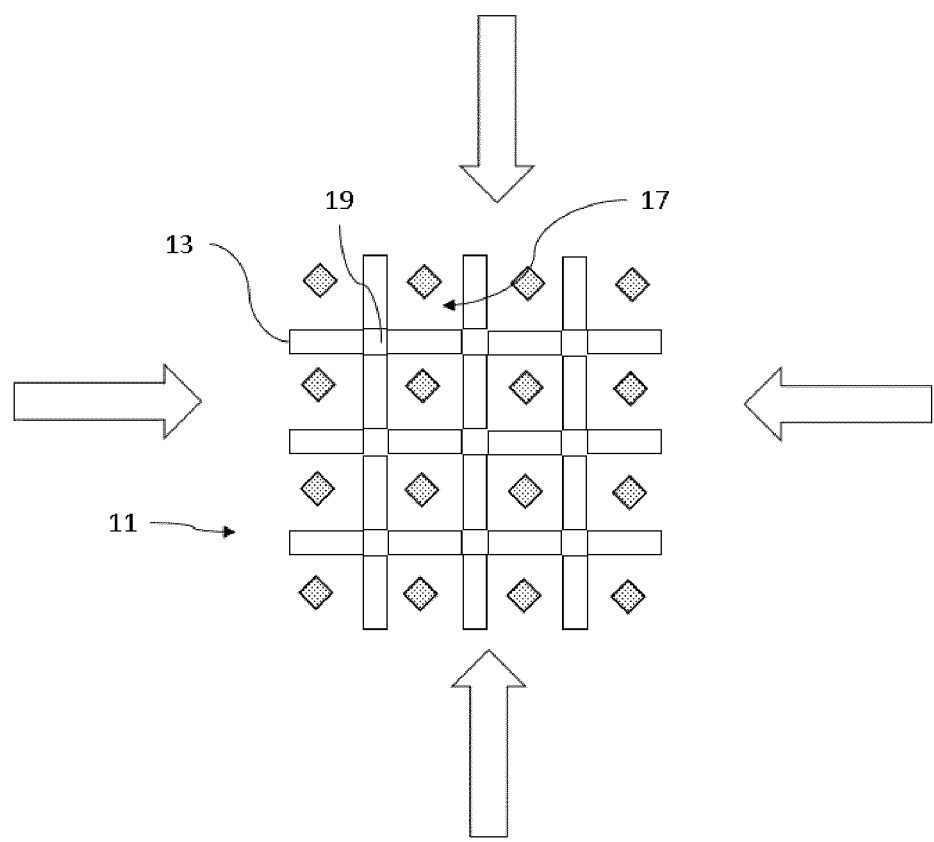
FIG. 11 illustrates intersection portions of core structures of a component according to an example.

FIG. 11 illustrates an alternative configuration of the intersection portion 19, in which the intersection portion does not comprise core structure material, or material having a refractive index which is the same as the core structure material. Instead, the intersecting portion comprises an optical gap (an optical discontinuity) between first and second portions of each of the plurality of first and second waveguides 13, in addition to the optical discontinuity 17. Light may be diverted out of the waveguides in the manner described in relation to FIG. 2. At the interface between the optical gap 19 and the core structure 11, a portion of light incident on the interface will likely be diverted from the propagation direction due to the difference in refractive index between the core structure and the optical gap. This may cause a greater portion of light which is propagating through the core structure to be coupled from, for example, the first waveguide to the second waveguide, where the light may then be coupled out of the core structure in the manner described in relation to the aforementioned examples.

A component may be manufactured according to the following steps: forming a redirection layer comprising at least one light redirection portion; forming a first cladding layer over the redirection layer (for example, the cladding may be spin coated); forming the core structure comprising at least one optical discontinuity at the first cladding layer (the core structure may be applied by screen printing the core structure material, moulding the core structure material, UV writing the core track into a spin coated core-material layer, using lithography, or by any other suitable method, the core structure may be embossed into the cladding, plasma etched, and/or photolithography may be used, or any other suitable method may be used. Alternatively, the pattern may be formed over the upper surface of the cladding); and a second cladding layer may be formed over the core structure.

The component may then be formed by methods such as overmoulding with the optically transparent material as a part of the mouthpiece. Alternatively a separate cover cladding can be applied before overmolding with the mouthpiece to allow wider material choice for the mouthpiece. A stiffener could be added or a thicker substrate material could be used. The optically transparent material may be different to the cladding or the same as the cladding.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein may be used in the practice or testing of the embodiments.

Although only a few exemplary embodiments have been described in detail above, those skilled in the art will readily appreciate that many modifications are possible in the exemplary embodiments without materially departing from the novel teachings and advantages of the embodiments of the present disclosure. The above-described embodiments of the present invention may advantageously be used independently of any other of the embodiments or in any feasible combination with one or more others of the embodiments Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements. In a device or apparatus claim enumerating several means, several of these means may be embodied by one and the same item of hardware. The mere fact that certain measures are recited in mutually different dependent claims does not indicate that a combination of these measures cannot be used to an advantage.

The invention claimed is:

1. A mouthpiece component for use in an intra oral illumination system, comprising:
   a core structure which defines at least one waveguide for receiving light which is directable at least partly by the waveguide along at least one light path of the core structure, wherein each at least one light path defines a propagation direction for light in a propagation plane;
   at least one optical discontinuity which is configured to cause at least a portion of light propagating along the light path in the at least one waveguide to be transmitted out of the at least one core structure and continue to propagate substantially parallel to the propagation plane; and
   at least one light redirection portion which is configured to redirect at least a portion of light which has been transmitted out of the core structure out of the propagation plane,
   wherein the at least one waveguide comprises a first waveguide and a second waveguide which define a first light path and a second light path respectively, and wherein the first light path and the second light path intersect at an intersection portion, wherein the optical discontinuity is in or is adjacent to the intersection portion.

2. The mouthpiece component as claimed in claim 1, wherein the intersection portion of the first waveguide and the second waveguide comprises material having the same refractive index as the core structure.

3. The mouthpiece as claimed in claim 1, wherein a shape of the intersection portion in a plane defined by the first and second waveguides comprises at least one of: a circle, an ellipse, a polygonal shape.

\* \* \* \* \*